United States Patent [19]

Watkins et al.

[11] Patent Number: 5,399,693
[45] Date of Patent: Mar. 21, 1995

[54] SUBSTITUTED PIPERAZINE-2-CARBOXYLIC ACIDS AND DERIVATIVES THEREOF

[75] Inventors: Jeffrey C. Watkins, Bristol; Arwel W. Jones, Chipping Sodbury, both of England

[73] Assignee: British Technology Group Limited, London, England

[21] Appl. No.: 469,819

[22] Filed: Jan. 23, 1990

Related U.S. Application Data

[63] Continuation of Ser. No. 274,677, Nov. 21, 1988, abandoned, which is a continuation of Ser. No. 721,656, Apr. 10, 1985, abandoned.

[30] Foreign Application Priority Data

Apr. 17, 1984 [GB] United Kingdom ............... 8409980
Apr. 27, 1984 [GB] United Kingdom ............... 8410865

[51] Int. Cl.$^6$ ............ C07F 9/6509; C07F 5/04; C07D 241/04; C07D 403/06
[52] U.S. Cl. ............ 544/337; 544/69; 544/121; 544/229; 544/295; 544/353; 544/354; 544/355; 544/356; 544/367; 544/370; 544/388; 544/389
[58] Field of Search .......... 544/69, 121, 229, 295, 544/337, 388, 389, 356

[56] References Cited

U.S. PATENT DOCUMENTS

| | | | |
|---|---|---|---|
| 3,028,388 | 4/1962 | Clarke ........................ | 544/388 |
| 3,751,416 | 8/1973 | Allen et al. ................. | 544/372 |
| 3,839,336 | 10/1974 | Borck et al. ............... | 544/371 |

(List continued on next page.)

FOREIGN PATENT DOCUMENTS

| | | |
|---|---|---|
| 134177 | 9/1976 | Denmark . |
| 0068544 | 1/1983 | European Pat. Off. . |
| 58495 | 10/1980 | Finland . |

(List continued on next page.)

OTHER PUBLICATIONS

Davies, et al, Chem. Abstracts, vol. 102, 1985, entry 89998b.

(List continued on next page.)

*Primary Examiner*—Emily Bernhardt
*Attorney, Agent, or Firm*—Nixon & Vanderhye

[57] ABSTRACT

Compounds of the general formula

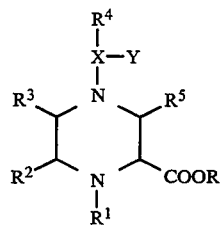

I wherein X is a $C_1$–$C_6$, straight chain saturated or unsaturated hydrocarbyl group, the group $R^4$ and the group Y are situated in any position in this chain and wherein at least one of the hydrogen atoms in X can be a heavy isotope of hydrogen;

$R^4$ is hydrogen or an alkyl, alkoxy, hydroxy, aryl, aryloxy, aralkyl, aralkoxy, aralkylamino, or morpholino group wherein the alkyl or aryl part of any one of said groups may be substituted by one or more halogeno groups; or $R^4$, together with at least one carbon atom of the group X, forms a carbocyclic or heterocyclic ring of 5 to 6 ring atoms;

Y is an acidic or related group giving rise to one or more electronegative sites in the group; or $R^4$—X—Y represents a carboxylic acyl group;

R is hydrogen or an alkyl, haloalkyl, aryl, haloaryl, aralkyl or haloaralkyl;

$R^1$ is hydrogen or an alkyl, haloalkyl, aryl, haloaryl, aralkyl or haloaralkyl group;

$R^2$ $R^3$ and $R^5$ which may be the same or different is each hydrogen or an alkyl, hydroxy, alkoxy, carboxy, alkyloxycarbonyl, halo, aryl, haloaryl or aryloxycarbonyl group; or $R^2$ and $R^3$ together with the carbon atoms to which they are attached form a ring system or $R^3$ and $R^4$ together and/or $R^3$ and X together form one or more than one ring systems, or a physiologically acceptable salt thereof have activity in the central nervous system.

14 Claims, No Drawings

U.S. PATENT DOCUMENTS

| | | | |
|---|---|---|---|
| 3,899,491 | 8/1975 | Ramey et al. | 544/231 |
| 3,926,999 | 12/1975 | Poetsch | 544/392 |
| 4,089,958 | 5/1978 | Freed et al. | 544/346 |
| 4,198,509 | 4/1980 | Losee et al. | 544/388 |
| 4,307,095 | 12/1981 | Silvestrini et al. | 514/214 |
| 4,338,317 | 7/1982 | Temple, Jr. et al. | 514/255 |
| 4,400,330 | 8/1983 | Wong et al. | 562/18 |
| 4,492,651 | 1/1985 | Sarantakis | 530/321 |
| 4,705,781 | 11/1987 | Boast | 514/85 |
| 4,880,808 | 11/1989 | Van Daele et al. | 544/389 |
| 4,898,854 | 2/1990 | Hutchison et al. | 514/89 |
| 4,906,621 | 3/1990 | Hutchison et al. | 514/89 |
| 4,939,129 | 7/1990 | Dixon et al. | 514/85 |
| 5,095,009 | 3/1992 | Whitten et al. | 514/85 |

FOREIGN PATENT DOCUMENTS

| | | |
|---|---|---|
| 69074 | 8/1985 | Finland . |
| 386897 | 8/1976 | Sweden . |
| 395455 | 8/1977 | Sweden . |
| 397531 | 11/1977 | Sweden . |
| 437663 | 3/1985 | Sweden . |
| 447256 | 11/1986 | Sweden . |
| 2104078 | 3/1983 | United Kingdom . |
| 2104079 | 3/1983 | United Kingdom . |

OTHER PUBLICATIONS

Evans, et al, Chem. Abstracts, vol. 87, 1977, entry 161505e.

Davies et al, *Br. J. Pharmacology*, p. 1 (1980).

Curtis and Watkins, Pharm. Rev. 1965, 17, 347–391.

Davies et al, Neurotransmitters and their receptors, Littauer (Editor), Wiley, Chichester, 1980, 333–347.

Davies et al, Journal of Neurochemistry, 1981, 36, 1305–1307.

Watkins, Glutamate: Transmitter in the Central Nervous System; Roberts et al., (Editor), Wiley, Chichester, 1981, 1–24.

Olverman et al., Nature, 1984, 307, 460–462.

Jucker et al, Chemical Abstracts, vol. 58, No. 8 (1963) col. 7935h 7937d.

Shishkin et al. Chemical Abstracts, vol. 90, No. 15 (1979) Abstract No. 121541u.

Davies et al Neuroscience Letters, 52, 79–84 (1984).

Davies et al Brain Research, 235, 378–386 (1982).

Davies et al. Experimental Brain Research, 49, 280–290 (1983).

Evans et al. British Journal of Pharmacology, 75, 65–75 (1982).

Jones et al Neuroscience, 13(2), 573–581 (1984).

Watkins et al. Annual Review of Pharmacology and Toxicology, 21, 165–204 (1981).

Davies et al Neurochemial Research, 7(9), 1119–1133 (1982).

Davies et al Comp. Biochem. Physiol., 72c, 211–224 (1982).

Mewett et al. CNS Receptors-From Molecular Pharmacology to Behavior, P. Mandel and F. V. DeFeudis (Eds)., 163–173 (1983).

Jones et al Proceedings of the Physiological Society, 18–19 Feb. 1983. (Abstract).

Ganong et al Society for Neuroscience, 10, 228 (1984). (Abstract).

Davies et al, 2–Amino–5–phosphonovalerate (2APV), a highly potent and specific antagonist at spinal NMDA receptors, British Journal of Pharmacology, 1980, 70, 52–53.

Davies et al, Chemical Abstracts, vol. 92, No. 158073 (1980).

Davies et al, Chemical Abstracts, vol. 94, No. 76577 (1981).

Bettinetti et al, Chemical Abstracts, vol. 57, No. 11195 (1962).

SUBSTITUTED PIPERAZINE-2-CARBOXYLIC ACIDS AND DERIVATIVES THEREOF

This is a continuation of application Ser. No. 07/274,677, filed Nov. 21, 1988, which was abandoned upon the filing hereof, which is a continuation of application Ser. No. 06/721,656, filed Apr. 10, 1985, which was abandoned upon the filing hereof.

THIS INVENTION relates to new organic compounds and more particularly, new 4-substituted piperazine-2-carboxylic acids of interest as agents influencing the central nervous system, their preparation, pharmaceutical compositions containing them and the compounds for use in methods of therapy practised on the human or animal body.

Various amino acids have recently become of interest following the discovery that they are able to influence the activity of certain receptor sites in the central nervous system and attention has been directed to the identification of materials that will have specific action in relation to these receptor sites with a view of identifying compounds that can be used to control various involuntary muscular activity and/or mental and/or affective disorders resulting from central nervous system malfunction.

We have now found that certain 4-substituted piperazine-2-carboxylic acids, which is a type of structure not previously investigated in relation to such activity, do act as depressants of electrical activity at certain receptor sites of the central nervous system.

Accordingly, the present invention provides compounds of the general formula:

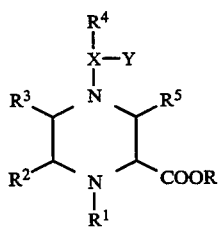
I wherein X is a $C_1$–$C_6$, preferably a $C_1$–$C_4$ straight chain saturated or unsaturated hydrocarbyl group, the group $R^4$ and the group Y are situated in any position in this chain and wherein at least one of the hydrogen atoms in X can be a heavy isotope of hydrogen.

The group $R^4$ is hydrogen or an alkyl, alkoxy, hydroxy, aryl, aryloxy, aralkyl, aralkoxy, aralkylamino, or morpholino group wherein the alkyl or aryl part of any one of said groups may be substituted by one or more halogeno groups; or wherein $R^4$, together with at least one carbon atom of the group X forms a carbocyclic or heterocyclic zing of 5 to 6 ring atoms;

Y is an acidic or related group giving rise to one or more electronegative sites in the group, usually:

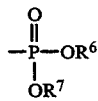
IIa or

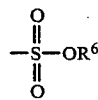
IIb or

IIc or

IId or

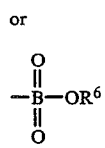
IIe where $R^6$ and $R^7$ which may be the same or different each is hydrogen or an alkyl, haloalkyl, aryl, haloaryl, aralkyl or haloaralkyl group; or wherein

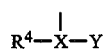

represents a carboxylic acyl group;

R can represent hydrogen or an alkyl, haloalkyl, aryl, haloaryl, aralkyl or haloaralkyl residue;

wherein $R^1$ is hydrogen or an alkyl, haloalkyl, aryl, haloaryl, aralkyl or haloaralkyl group:

wherein $R^2$, $R^3$ and $R^5$ which may be the same or different, may each be hydrogen or an alkyl, hydroxy, alkoxy, carboxy, alkyloxycarbonyl, halo, aryl, haloaryl or aryloxycarbonyl group; or wherein $R^2$ and $R^3$ together with the carbon atoms to which they are attached form a ring system or wherein $R^3$ and $R^4$ together and/or $R^3$ and X together form one or more than one ring systems.

In the compounds of the invention it is preferred that X represents a $C_3$ chain as the indications are that such compounds give rise to the more active compounds. However, compounds of interest can also be secured where X is a $C_1$, $C_2$ $C_4$, $C_5$ or $C_6$ straight chain of carbon atoms.

Other compounds of interest are those where X is an unsaturated residue and interest here centres particularly upon those compounds containing a chain of three carbon atoms with one site of carbon-to-carbon unsaturation. The synthetic methods that we adopt lend themselves most readily to the production of compounds containing one olefinic double bond and this may be located between the two carbon atoms nearest to the piperazine ring or between the two carbon atoms furthest from the piperazine ring.

Compounds in which at least one of the hydrogen atoms in the X residue represents a heavy isotope of hydrogen are of particular interest in tracer experiments. Such radio-active compounds will normally contain two heavy hydrogen atoms since such compounds are most easily prepared by hydrogenation of a compound of the invention containing an olefinic double bond in the group X using tritium.

Our previous investigations with acyclic amino acids have shown that the acidic group represented by the group Y is preferably a phosphonic acid or ester thereof and the same preference exists in the piperazine carboxylic acids of the present invention. Whether the phosphonic acid is present in the mono- or di-ester form or in the free acid form will be governed partly by the manner in which it is desired to use the compound since, while the indications are that it is the free acid form of the compound that exhibits the best activity, certain lipophilic residues are advantageous in the compound to secure passage of the compound through the blood brain barrier to direct the compound to its ultimate site of activity. The present indications therefore are that while in vitro activity is best demonstrated by compounds in which $R^6$ and $R^7$ are both hydrogen, for certain clinical uses it is preferred that one or both of $R^6$ and $R^7$ represent an organic residue of the type defined above. When $R^6$ and/or $R^7$ represents an alkyl group, it is preferred that this contains 1 to 6 and particularly 1 to 4 carbon atoms and methyl, ethyl, n-propyl and n-butyl esters are of interest. When $R^6$ and/or $R^7$ is an aryl group, it is preferred that this is a phenyl group although, in certain circumstances, polynuclear aryl residues such as naphthyl residues are of interest because of their effect on the hydrophilic/lipophilic balance of the compound. The hydrophilic/lipophilic balance of the compound can also be influenced by the presence or absence of any halogeno substituents present and here, mention may be made of fluoro, chloro or bromo substitution.

As an alternative to a phosphonic acid residue as the group Y, compounds of the present invention can contain a sulphonic, sulphinic, carboxylic or boronic acid residue and, as mentioned above, these acid residues can be present in free acid form or in an ester form, similar considerations applying to the presentation of the compound in free acid or ester form and, in the latter case, to the selection of the esterifying residue.

Further alternative groups for Y may include phenol or uracil, or hydantoin, or barbituric acid or isoxazole, or oxadiazolidindione residues, or other groups providing similar electronegative sites.

The residue $R^4$ in the compounds of the invention is also introduced to influence the hydrophilic/lipophilic balance of the compound. In the simplest compounds of the present invention, $R^4$ will be hydrogen but alternative structures include compounds where $R^4$ represents an alkyl or alkoxy group normally containing up to 6 carbon atoms and preferably containing i to 4 carbon atoms such as a methyl, ethyl, n-propyl or n-buryl group. When $R^4$ represents an alkoxy group, the alkoxy group may contain 1 to 6 and preferably I to 4 carbon atoms such as methoxy, ethoxy, n-propoxy or n-butoxy. $R^4$ may also be a hydroxy group. When $R^4$ is an aryl, aryloxy, aralkyl, aralkoxy or aralkylamino group, the aryl residue is preferably a phenyl residue although the aryl residue may also be a polynuclear residue such as naphthyl. Aralkyl, aralkoxy and aralkylamino residues may be residues in which the alkyl portion contains 1 to 6 and preferably 1 to 4 carbon atoms. The alkyl or aryl residue in these compounds may be substituted by at least one halogeno group such as a fluoro, chloro or bromo group. The hydrophilic/lipophilic balance of the compounds of the invention can also be favourably influenced by the presence of a morpholino substituent as the group $R^4$.

R can represent hydrogen or an alkyl, haloalkyl, aryl, haloaryl, aralkyl or haloaralkyl residue. When R represents an alkyl group, it may contain 1 to 6 and preferably 1 to 4 carbon atoms and the aryl residue may be phenyl or a polynuclear residue such as naphthyl. Alkyl or aryl residues may also be substituted by one or more halogeno groups such as fluoro, chloro or bromo groups. The group R may be identical to the group $R^6$ and/or $R^7$ and the synthetic methods adopted often will most easily give compounds in which the groups R, $R^6$ and, when present, $R^7$ are identical.

$R^1$ may also represent hydrogen or an alkyl, haloalkyl, aryl, haloaryl, aralkyl or haloaralkyl group and, as for the group R, the alkyl groups may contain 1 to 6, preferably 1 to 4 carbon atoms and the aryl groups may be phenyl or polynuclear residues such as naphthyl. When halogeno substituents are present, they may be one or more fluoro, chloro or bromo substituents.

The groups $R^2$, $R^3$ and $R^5$ which may be the same or different, may each be hydrogen or an alkyl, hydroxy, alkoxy, carboxy, alkyloxycarbonyl, halo, aryl, haloaryl or aryloxycarbonyl group and once again, alkyl groups may contain 1 to 6 and preferably 1 to 4 carbon atoms and aryl Groups may be phenyl or polynuclear residues such as naphthyl. When substituents are present, these may be one or more fluoro, chloro or bromo groups. Alternatively, $R^2$ and $R^3$ may, together with the carbon atoms to which they are attached on the piperazine ring, form a ring system which may be of aromatic character such as a benzene ring so that the whole ring system is a 1,2,3,4-tetrahydro-quinoxaline which may be substituted.

When the groups R, $R^1$, $R^2$ and $R^3$ represent alkyl or substituted alkyl groups, it is preferred that the alkyl groups be methyl, ethyl, n-propyl or n-butyl.

When the group

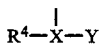

is a carboxylic acyl group, it may be derived from a carboxylic acid $R^8COOH$ where $R^8$ is a saturated or unsaturated aliphatic hydrocarbon residue containing up to 6 and preferably up to 4 carbon atoms or an aromatic ring, e.g. phenyl or naphthyl, where the aliphatic residue or aromatic ring can be unsubstituted or substituted by one or more halogeno, carboxy, hydroxy or $C_1$-$C_6$ alkoxy groups. Preferably, the carboxylic acyl group is derived from benzoic acid or a benzoic acid substituted in the ring by one or more F, Cl or Br groups.

When the compounds of the invention contain beth basic and acidic functions either or both of the basic and acidic functions can be prepared in the compounds of the invention in salt form. Thus, for formulation reasons, it is often desirable to prepare the 2-carboxylic acid residue and/or the acid residue Y in the form of a physiologically acceptable water-soluble salt such as the sodium salt. Compounds of the invention in which the groups COOR and Y are in the form of the free acid or an ester thereof or a salt thereof can be prepared in the form of salts of the basic amino groups and here, salts of interest are physiologically acceptable acid addition salts, such as salts with hydrochloric acid, acetic acid, succinic acid, tartaric acid, or citric acid.

The compounds of the invention will always contain a centre of asymmetry at $C_2$ and possibly elsewhere. The compounds of the present invention include both racemic mixtures and compounds in which $C_2$ is substantially completely in the R or substantially completely in the S configuration.

The compounds of the invention can be prepared by reacting a piperazine-2-carboxylic acid or ester of the formula III:

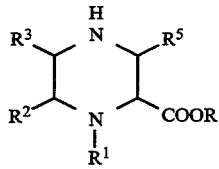

with a compound of formula IV

in which formulae R, $R^1$, $R^2$, $R^3$, $R^4$, $R^5$, X and Y are as defined above and Z represents a reactive group such as a halogeno group or p-tosyl group. This condensation reaction will normally be carried out under basic conditions. Where

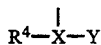

together represents or contains an acyl group, the compounds can be prepared by reaction of the piperazine with the corresponding acyl halide or other activated acyl precursor, again under basic conditions.

More specifically, compounds of the formula IV that may be used include compounds in which the acidic residues in the group Y are in the form of an ester. For example, in the preferred compounds of the invention in which Y represents a phosphonic acid residue, Y in the compound IV can be a phosphonic acid dialkyl ester. Following the condensation reaction, one or both of the ester groupings can be hydrolysed under acidic conditions if desired to give a corresponding invention compound in the form of the free phosphonic acid. When it is desired to prepare compounds in which the acidic residue Y is a sulphonic or sulphinic or carboxylic or boronic acid residue, the experimental methods we have adopted indicate the use of intermediates IV in which the group Y is in the free acid form. If the synthetic methods adopted result in the production of invention compounds in which the group Y is in free acid form, then these acidic groups can be subsequently esterified or converted into salts as desired. Alternatively, where phosphonic acid compounds are to be prepared, these will normally be prepared in the ester form, as indicated above, and if desired, the esters can be subsequently converted into free acid or salts and reconverted into alternative ester forms if required.

When it is desired to prepare invention compounds in which X contains carbon-to-carbon unsaturation, the intermediate IV can be one in which the group X contains corresponding carbon-to-carbon unsaturation. This will give rise to an invention compound having corresponding carbon-to-carbon unsaturation although occasionally it is found that migration of the carbon-to-carbon unsaturation occurs. Invention compounds containing carbon-to-carbon unsaturation in the group X can be used as such or can be regarded as intermediates for the production of invention compounds in which X represents a saturated group. Thus, the sites of unsaturation can be hydrogenated catalytically under conventional conditions either using hydrogen or using tritium to introduce sites in the molecule for tracer work.

It is usually convenient to use intermediates IV in which Z represents a reactive halogeno group, preferably chlorine or bromine but, as indicated above, other synthetic methods can be adopted for reaction at a basic nitrogen atom to introduce the group

onto the piperazine ring.

Intermediates III can be obtained by hydrogenation of the corresponding pyrazine carboxylic acids. This reduction will normally give rise to a compound that is racemic at $C_2$ but where individual isomers are required, resolution of hydrogenation products will be carried out prior to reaction with intermediate IV, or the final condensation products will be resolved.

When it is desired to produce the invention compounds in the form of salts, salt formation will normally be effected subsequent to reaction of III with IV, but some condensation reactions may give rise to salt products directly.

In accordance with a further feature of the invention, we provide a pharmaceutical composition comprising a compound of formula I in association with a pharmaceutically acceptable diluent or carrier. The compounds of the invention act on the central nervous system and may be administered parenterally or orally, e.g. intravenously for acute treatment, or subcutaneously or orally for chronic treatment. Compounds of the invention will be formulated for clinical use in suitable vehicles, normally as a preparation of a water-soluble salt, though preparations of low water solubility, possibly in association with physiologically tolerable emulsifying agents, may be used for depot administration.

Since it is believed to be necessary for compounds of the invention to penetrate the blood brain barrier, it is frequently necessary to administer the compounds of the present invention in amounts significantly in excess of the amounts necessary to be achieved within the brain for the therapeutic effect desired and this will influence the concentration of the active compounds in the compositions of the present invention. Considerations of this type suggest that compositions of the invention might contain the active compound in a concentration such that a conventional dosage volume would provide the subject with up to abut 200 mg/kg body weight although, when the compounds are to be administered by the intravenous or subcutaneous route, dosages in the region of about 1-20 mg/kg body weight are to be expected for the more active compounds and/or for those substances with a high lipophilic to hydrophilic balance.

In accordance with a further feature of the invention, we provide compounds of formula I for use in a method of therapy practised on the human or animal body. More specifically, the compounds of the invention have been found to antagonise responses of mammalian central neurones to excitatory amino acids and also to depress spontaneous and evoked synaptic activity in the central nervous system. Amino acid receptors mediate or modulate synaptic excitation of many excitatory synapses in the brain. The compounds of the present invention can modify abnormal central nervous system activity involving amino acid receptors and consequently are of interest in providing beneficial intervention in cases where such abnormalities arise.

The following Examples are given to illustrate the invention. Temperatures are in °C.

EXAMPLE 1

Synthesis of 3-((±)-2-carboxypiperazin-4-yl)propyl-1-phosphonic acid (CPP)

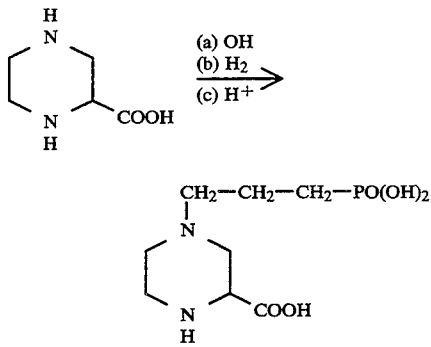

(a) Ethyl 3-((±)-2-carboxypiperazin-4-yl)-propenyl-1-phosphonate

To a solution of piperazine-2-carboxylic acid (8 g, 0.06 mole) in water (50 ml) containing sodium hydroxide (7.2 g, 0.18 mole) was added diethyl 3-bromo-prop-2-enyl-1-phosphonate (15.75 g, 0.06 mole). The resulting solution was stirred and maintained at 65°–70° for 12 h. The solution was allowed to cool, neutralized with dilute hydrochloric acid to pH 7, and applied to Dowex 50 H+ resin. The ninhydrin-positive aqueous eluates were combined and evaporated under reduced pressure to yield 9 g of a white solid which was used in the next step without further purification.

(b) Ethyl 3-((±)-2-carboxypiperazin-4-yl)-propyl-1-phosphonate

A solution of the product of step (a) (3.0 g) in 7M aqueous ammonia solution (50 ml) was hydrogenated over 5% palladium on charcoal (1 g) at room temperature and atmospheric pressure until no more hydrogen was taken up. The resulting solution was evaporated under reduced pressure to yield ethyl 3-((±)-2-carboxypiperazin-4-yl)-propyl-1-phosphonate. (4.8 g). Recrystallization from ethanol gave a white solid, m.p. 140°–40°.

Calculated for $C_{10}H_{21}N_2O_5P$: C, 42.8; H, 7.5; N, 10.0% Found: C, 42.8; H, 7.6; N, 9.8%.

(c) 3-((±(-2-Carboxypiperazin-4-yl)-propyl-1-phosphonic acid

A solution of ethyl 3-((±)-2-carboxypiperazin-4-yl)-propyl-1-phosphonate (4.7 g) was taken up into 6M hydrochloric acid (100 ml) and the resulting solution was boiled under reflux for 2 h. The solution was evaporated to dryness and the residue was taken up into minimum volume of water for application to a Dovex AG-1-acetate resin column. The product, 3-((±)-2-carboxypiperazin-4-yl)-propyl-1-phosphonic acid, was eluted from the resin with 0.1M acetic acid. Following evaporation of the eluate, the residue was recrystallized from aqueous ethanol yielding 3.9 g of a white solid, m.p. 174°–5°.

Calculated for $C_8H_{17}N_2O_5P.1H_2O$: C, 35.5; H, 7.1; N, 10.4% Found: C, 35.9; H, 7.5; N, 10.0%.

EXAMPLE 2

Synthesis of 3-(±)-2-carboxypiperazin-4-yl)-propane-1-sulphonic acid (CPS)

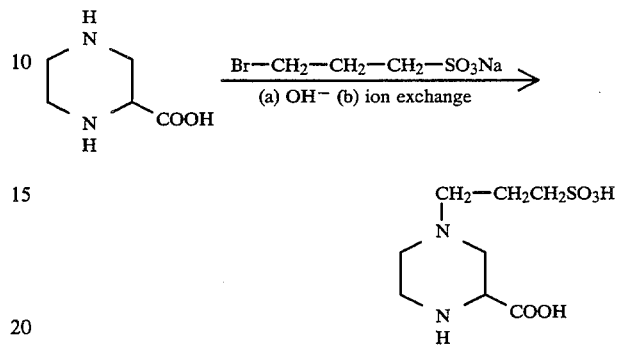

Sodium 3-bromo-propane-1-sulphonate (2.25 g, 0.01 mole) was added to a solution of piperazine-2-carboxylic acid (1.3 g, 0.01 mole) in aqueous sodium hydroxide (0.9 g NaOH/30 ml H2O). The resulting solution was maintained at 60°–65° for 12 h. The product, 3((±)-2-carboxypiperazin-4-yl)-propane-1-sulphonic acid, was isolated by passage of the reaction mixture through Dowex-AG-1-acetate resin. Evaporation of the column filtrate and aqueous washings and recrystallization of the crude product from a 50% aqueous ethanol solution yielded 3-((±)-2-carboxy-piperazin-4-yl)-propane-1-sulphonic acid (500 mg) as a white crystalline solid, m.p. 190°–191°.

Calculated for $C_8H_{16}N_2O_5S.1H_2O$: C, 35.5; H, 6.7; N, 10.4% Found: C, 35.8; H, 6.8; N, 10.2%.

EXAMPLE 3

Synthesis of 2-((±)-2-carboxypiperazin-4-yl)-propionic acid

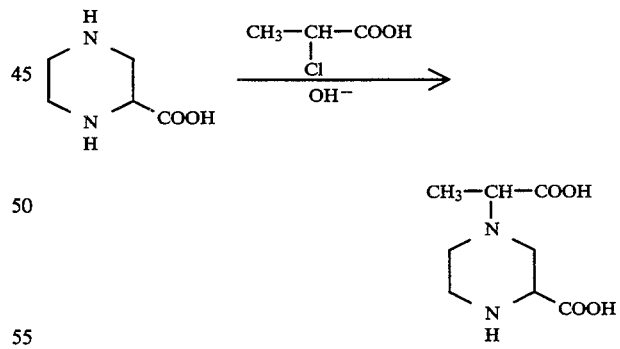

Piperazine-2-carboxylic acid (1.3 g, 0.01 mole) and 2-chloropropionic acid (1.1 g, 0.01 mole) were dissolved in aqueous sodium hydroxide solution (0.9 g NaOH/20 ml H2O) and the resulting solution was maintained at 60°–65° for 12 h. The product was isolated by ion-exchange chromatography on Dowex AG-1-acetate resin with elution by 0.3M acetic acid. Recrystallization from 50% aqueous ethanol yielded 2-((±)-2-carboxypiperazin-4-yl)-propionic acid (520 mg) as a white solid, m.p. 173°–4°.

Calculated for $C_8H_{14}N_2O_4{\frac{1}{2}}H_2O$: C, 45.9; H, 7.2; N, 13.3% Found: C, 45.7; H, 7.5; N, 13.6%.

EXAMPLE 4

Synthesis of 4-(4-bromobenzoyl)-piperazine-2,3-dicarboxylic acid (BBP)

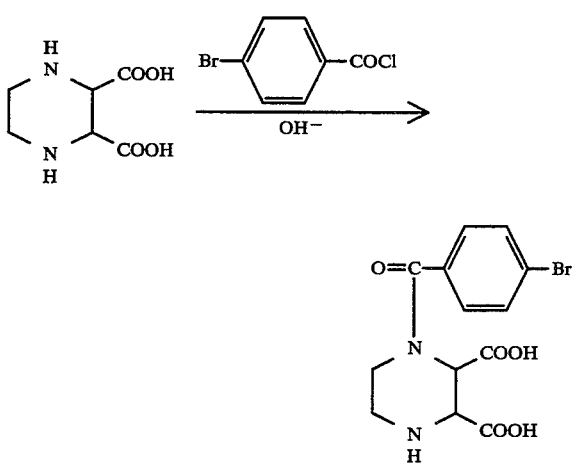

To an ice cold solution of piperazine-2,3-dicarboxylic acid (1.74 g/0.01 mole) in aqueous sodium hydroxide (1.2 g/20 ml) was added 4-bromobenzoyl chloride (2.2 g/0.01 mole) over S0 min. The resulting solution was stirred at 0° for 2 h, then allowed to warm to room temperature overnight. The solution was applied to a column of Dowex AG-1-acetate resin and the ninhydrin positive fractions of the 3M acetic acid eluate were combined and evaporated to dryness. Recrystallization of the residue from a 50% aqueous ethanol solution yielded 4-(4-bromobenzoyl)-piperazine-2,3-dicarboxylic acid (800 mg) as a white solid m.p., 218°-20°.

Calculated for $C_{13}H_{13}N_2O_5Br$: C, 43.7; H, 3.7; N, 7.8% Found: C, 43.4; H, 3.8; N, 7.8%.

The following list gives further examples of compounds of the invention which have been made using the methods of Examples 1 to 4 above, or modification thereof, using correspondingly substituted reagents III and IV.

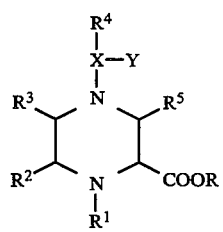

| Method as in Example No. | $R,R^1$ $R^2,R^3$ | $R^4$ \| —X—Y | $R^5$ | Formula | N Calc. | N Found | m.p. (°C.) | HVE[a] |
|---|---|---|---|---|---|---|---|---|
| 1 | H | —(CH₂)₃—PO(OH)₂ | H | $C_8H_{17}N_2O_5P.(1H_2O)$ | 10.4 | 10.1 | 174–5 | 0.2 |
| 1 | H | —(CH₂)₃—PO(OH)OC₂H₅ | H | $C_{10}H_{21}N_2O_5P$ | 10.0 | 9.8 | 140–4 | 0.1 |
| 1[b] | H | —(CH₂)₂—PO(OH)₂ | H | $C_7H_{15}N_2O_5P.(2H_2O)$ | 10.2 | 10.1 | 197–8 | 0.6 |
| 1[b] | H | —(CH₂)₂—PO(OH)OC₂H₅ | H | $C_9H_{19}N_2O_5P(1H_2O)$ | 9.9 | 10.0 | — | 0.5 |
| 1[b,c] | H | —(CH₂)₂—PO(OH)₂ | COOH | $C_8H_{15}N_2O_7P(1H_2O)$ | 9.3 | 8.7 | 224–6 | 2.6 |
| 2 | H | —(CH₂)₃—SO₃H | H | $C_8H_{16}N_2O_5S(1H_2O)$ | 10.4 | 10.2 | 190–1 | 0.8 |
| 2 | H | —(CH₂)₂SO₃H | H | $C_7H_{14}N_2O_5S(1H_2O)$ | 10.9 | 10.9 | 226–7 | — |
| 3 | H | —CH₂—COOH | H | $C_7H_{12}N_2O_4(½H_2O)$ | 14.2 | 14.0 | 178–9 | 0.48 |
| 3 | H | CH₃—CH—COOH \| | H | $C_8H_{14}N_2O_4(½H_2O)$ | 13.3 | 13.6 | 173–4 | 0.1 |
| 3 | H | —(CH₂)₂—COOH | H | $C_8H_{14}N_2O_4(½H_2O)$ | 13.3 | 13.3 | 172–3 | 0.1 |
| 3 | H | —(CH₂)₃—COOH | H | $C_9H_{16}N_2O_4$ | 13.0 | 13.1 | — | 0.37 |
| 3 | H | —CH₂— (heterocyclic group) | H | $C_{10}H_{14}N_4O_4$ | 22.0 | 21.9 | 285–7 | 0 |
| 3 | H | —CH₂—COOH | COOH | $C_8H_{12}N_2O_6$ | 12.0 | 11.7 | 260–1 | 2.1 |
| 3 | H | —(CH₂)₃COOH | COOH | $C_{10}H_{16}N_2O_6$ | 10.8 | 11.3 | 197–9 | 2.0 |

-continued

The following list gives further examples of compounds of the invention which have been made using the methods of Examples 1 to 4 above, or modification thereof, using correspondingly substituted reagents III and IV.

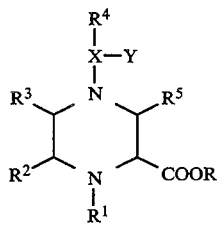

| Method as in Example No. | R,R¹ R²,R³ | $\overset{R^4}{\underset{-X-Y}{|}}$ | R⁵ | Formula | N Calc. | N Found | m.p. (°C.) | HVE[a] |
|---|---|---|---|---|---|---|---|---|
| 3 | H | —CH₂—C(=NH—CO—)=N(H)— (ring with C=O) | COOH | $C_{11}H_{14}N_4O_6$ | 18.8 | 18.4 | 291–3 | 1.7 |
| 4[d] | H | —CO—(CH₂)₂—COOH | H | $C_9H_{14}N_2O_5$ | 12.2 | 11.8 | 217–8 | 0.35 |
| 4 | H | —CO—C₆H₅ | COOH | $C_{13}H_{14}N_2O_5$ | 10.1 | 10.1 | 185–6 | 1.9 |
| 4 | H | —CO—C₆H₄—Cl (para) | COOH | $C_{13}H_{13}N_2O_5Cl(\tfrac{1}{2}H_2O)$ | 8.7 | 8.6 | 216–7 | 1.6 |
| 4 | H | —CO—C₆H₄—Br (para) | COOH | $C_{13}H_{13}N_2O_5Br$ | 7.8 | 7.8 | 218–220 | 1.9 |
| 4[e] | H | —CO—C₆H₄—COOH (ortho) | COOH | $C_{14}H_{14}N_2O_7(1H_2O)$ | 8.2 | 8.1 | 227–9 | 2.5 |
| 4 | H | —CO—C₆H₄—Cl (meta) | COOH | $C_{13}H_{13}N_2O_5Cl$ | | | | |
| 4 | H | —CO—C₆H₄—Cl (ortho) | COOH | $C_{13}H_{13}N_2O_5Cl$ | | | | |
| 4 | H | —CO—C₆H₃—Cl₂ | COOH | $C_{13}H_{12}N_2O_5Cl_2$ | | | | |

[a] Anionic mobility in high voltage paper electrophoresis (4000 V, 72 V/cm, 0.2M NaOAc buffer, pH 4.0, 20 min.) relative to L-glutamate = 1.0
[b] Halogeno reactant IV saturated; no hydrogenation step.
[c] Reactants heated at reflux temperature for 2 hours instead of at 60–65 for 12 hours.
[d] Succinic anhydride used as reactant IV
[e] Phthalic anhydride used as reactant IV The compounds of the invention have antagonist action at excitatory amino acid receptors in the central nervous system. There are several different types of these receptors, some or all of which are intimately involved in central nervous function. Three types of receptors that have been described in the neuroscientific literature are known as N-methyl-D-aspartate (NMDA), kainate (K) and quisqualate (Q) receptors. The compounds of the invention have differential actions at these receptors, some being more effective at NMDA receptors and others at K or Q receptors. Compounds which act at excitatory amino acid receptors can affect the action of natural amino acid transmitter substances and thereby influence the electrical activity of the central nervous system.

To evaluate actions of substances at amino acid receptors on nerve cells (neurones), the substances may be tested on spinal cord neurones, which have similar characteristics to nerve cells in the brain. Typically, the isolated spinal cord of the frog or 4–8 day old rat is used, and compounds are tested for their ability to affect the activity of spinal neurones induced by excitatory amino acids or by electrical stimulation of afferent fibres. Table 2 shows the relative potencies of some invention compounds relevant to previously known excitatory amino acid antagonists.

The most potent NMDA antagonism previously known were 2-amino-5-phosphonopentanoic acid (APS) and 2-amino-7-phosphonoheptanoic acid (AP7), and γ-D-glutamylglycine (γDGG) was one of the most potent previously known antagonists of kainate and quisqualate. From Table 2 it can be seen that the invention compound 3-((±)-2-carboxypiperazin-4-yl)-propyl-1-phosphonic acid (CPP) is more potent as an antagonist of NMDA and of polysynaptic spinal excitation than is either AP5 or AP7. The invention compound 4-(4-bromobenzoyl)-piperazine-2,3-dicarboxylic acid (BBP) is a more potent antagonist of kainate and quisqualate-induced depolarizations than is γDGG, and is also more potent as a depressant of monosynaptic excitation.

NMDA receptor antagonists have been shown to have anticonvulsant activity. Amongst known excitatory amino acid antagonists, AP7 was previously the most potent anticonvulsant. Table 3 shows that CPP has significantly higher anticonvulsant activity than AP7 when tested against 3-mercaptopropionate-induced convulsions in mice.

TABLE 2

Depression of synaptic excitation and of amino acid-induced motoneuronal depolarization in isolated hemisected spinal cord preparations.

| Test Compound | Conc. (μM) | Percent depression | | Amino Acid-Induced Depolarization[2] | | |
|---|---|---|---|---|---|---|
| | | MS | PS | NMDA | K | Q |
| γDGG | 700 | 24 | | 1.0[a,b] | 1.0[a,b] | 1.0[a,b] |
| AP5 | 2 | — | 27 | 0.18[a] 0.17[b] | 19.5[a] | 6.5[a] |
| AP7 | 3 | — | 28 | 0.21[a] 0.25[b] | 19.8[a] | 7.5[a] |
| CPP | 0.5 | — | 28 | 0.03[b] | 4.7[b] | 5.1[b] |
| CPS | 500 | 6 | 32 | | | |

TABLE 2-continued

Depression of synaptic excitation and of amino acid-induced motoneuronal depolarization in isolated hemisected spinal cord preparations.

| Test Compound | Conc. (μM) | Percent depression | | Amino Acid-Induced Depolarization[2] | | |
|---|---|---|---|---|---|---|
| | | MS | PS | NMDA | K | Q |
| BBP | 100 | 24 | 8 | 4.3[b] | 0.62[b] | 0.47[b] |

[1]Monosynaptic (MS) and polysynaptic (PS) excitation of motoneurones in the spinal cord from 4–8 day old rats was elicited by electrical stimulation of a dorsal root and recorded from the corresponding ventral root. Figures relate to the depression of the magnitude of the two components as measured respectively from oscilloscope traces and chart recorded traces.
[2]Amino acid-induced motoneuronal depolarization in frog (a) or 4–8 day old rat (b) spinal cord was maintained by NMDA (5 μM), kainate (2.5 μM) or quisqualate (2.5 μM) continuously present in the superfusion medium, and the relative abilities of invention and standard substances to reverse these depolarizations assessed from their effects when added to the superfusion medium in concentrations of 0.1 μM to 1 mM for periods of 2 min. Each substance was compared with γDGG (10 μM - 1 mM) as a standard antagonist known to be effective against all three agonists. Figures give relative concentrations of agonists to produce the same degree of reversal. The medium contained tetrodotoxin (0.1 μM).
Abbreviations:
γDGG, γ-D-glutamylglycine;
AP5 (±)-2-amino-5-phosphonopentanoic acid;
AP7, (±)-2-amino-7-phosphono-heptanoic acid;
CPP 3-((±)-2-carboxypiperazin-4-yl)-propane-1-phosphonic acid;
CPS 3-((±)-2-carboxypiperazin-4-yl) propane-1-sulfonic acid;
BBP, 4-(4-bromobenzoyl)-peperazine-2,3-dicarboxylic acid.

TABLE 3

Relative potencies of phosphono compounds as antagonists at neuronal NMDA receptors and as anticonvulsants

| Compound | Depression of NMDA-induced and synaptic excitation in rat spinal cord[1] | | Anti-convulsant Activity (mice)[2] |
|---|---|---|---|
| | NMDA | Synaptic | |
| AP5 | 1.0 | 1.0 | 0.1 |
| AP7 | 0.75 | 0.75 | 1.0 |
| CPP | 6 | 4 | 2.5–5.0 |

[1]Relative potencies of substances as antagonists of NMDA-induced motoneuronal depolarization and as depressants of spontaneous and dorsal root-evoked ventral root synaptic potentials in spinal cord of 4-day-old rat; bath administration of drugs.
[2]Relative anticonvulsant potencies of substances in mice injected with 3-mercaptopropionic acid (3-MP), 100 mg/kg; 3-MP and the phosphonates injected subcutaneously.
Abbreviations:
NMDA = N-methyl-D-aspartic acid
AP5 = DL-2-amino-5-phosphonopentanoic acid
AP7 = DL-2-amino-7-phosphonoheptanoic acid
CPP = 3-((±)-2-carboxypiperazin-4-yl)-propyl-1-phosphonic acid (general formula I, $R=R^1=R^2=R^3=R^4=R^5=R^6=R^7=H$;
$X=-CH_2-CH_2-CH_2-$; $Y=PO_3H_2$)

We claim:
1. A compound of the formula:

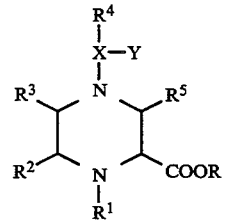

wherein X is $C_1$–$C_6$ straight chain saturated or monounsaturated hydrocarbyl, $R^4$ and Y are situated in any position in X and wherein at least one of the hydrogen atoms in X can be heavy isotope of hydrogen;
  $R^4$ is hydrogen or alkyl, alkoxy, hydroxy, aryl, aryloxy, aralkyl, aralkoxy, aralkylamino, or morpholino wherein the aryl moieties are phenyl or naphthyl, the alkyl moieties have from 1 to 6 carbon atoms, and the alkyl and aryl moieties are optionally substituted by one or more halogeno selected from fluoro, chloro and bromo; and Y is selected from:

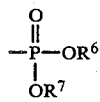  IIa or

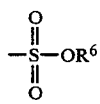  IIb or

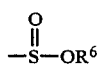  IIc or

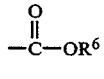  IId or

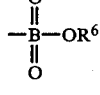  IIe where $R^6$ and $R^7$, which may be the same or different, is each hydrogen or alkyl, aryl, or aralkyl, wherein the aryl moieties are phenyl or naphthyl, the alkyl moieties have 1 to 6 carbon atoms, and the alkyl and aryl moieties are optionally substituted by one or more halogeno selected from fluoro, chloro and bromo, or Y is a 6-uracil residue; or

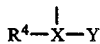

represents —CO—$R^8$ wherein $R^8$ is saturated or unsaturated $C_1$-$C_6$ aliphatic hydrocarbyl, phenyl or naphthyl, optionally substituted by one or more halogeno selected from fluoro, chloro and bromo, carboxy, hydroxy or $C_1$-$C_6$ alkoxy;

R is hydrogen or alkyl, aryl or aralkyl wherein the aryl moieties are is]phenyl or naphthyl, the alkyl moieties have 1 to 6 carbon atoms, and the alkyl and aryl moieties are optionally substituted by one or more halogeno selected from fluoro, chloro and bromo;

$R^1$ is hydrogen or alkyl, aryl, or aralkyl wherein the aryl moieties are phenyl or naphthyl, the alkyl moieties have from 1 to 6 carbon atoms, and the alkyl and aryl moieties are optionally substituted by one or more halogeno selected from fluoro, chloro and bromo;

$R^2$, $R^3$ and $R^5$ which may be the same or different is each hydrogen or alkyl, hydroxy, alkoxy, carboxy, alkyloxycarbonyl, halogeno selected from fluoro, chloro, bromo, aryl, or aryloxycarbonyl wherein the aryl moieties have 1 to 6 carbon atoms, and the aryl moieties are optionally substituted by one or more halogeno selected from fluoro, chloro and bromo;

or a physiologically acceptable salt thereof.

2. A compound as claimed in claim 1 wherein Y is a phosphonic acid or ester thereof.

3. A compound as claimed in claim 1 in which R, $R^1$, $R^2$, $R^3$, $R^4$ and $R^5$ are each hydrogen.

4. A compound which is 3-((±)-2-carboxypiperazin-4-yl)propyl-1-phosphonic acid.

5. A compound which is ethyl-3-((±)-2-carboxypiperazin-4-yl)propenyl-1-phosphonate.

6. A compound of the formula:

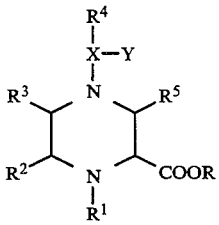

wherein X is $C_1$-$C_4$ straight chain saturated or mono-unsaturated hydrocarbyl, $R^4$ and Y are situated in any position in X and wherein at least one of the hydrogen atoms in X and wherein at least one of the hydrogen atoms in X can be a heavy isotope of hydrogen;

$R^4$ is hydrogen or alkyl, alkoxy, hydroxy, aryl, aryloxy, aralkyl, aralkoxy, aralkylamino, or morpholino wherein the aryl moieties are phenyl or naphthyl, the alkyl moieties have from 1 to 6 carbon atoms, and the alkyl and aryl moieties are optionally substituted by one or more halogeno selected from fluoro, chloro and bromo; and Y is selected from:

  IIa or

  IIb or

  IIc or

  IId or

  IIe where $R^6$ and $R^7$ which may be the same or different is each hydrogen or alkyl, aryl, or aralkyl, wherein the aryl moieties are phenyl or naphthyl, the alkyl moieties have 1 to 6 carbon atoms, and the alkyl and aryl moieties are optionally substituted by one or more halogeno selected from fluoro, chloro and bromo, or Y is a 6-uracil residue;

R is hydrogen or alkyl, aryl or aralkyl wherein the aryl moieties are phenyl or naphthyl, the alkyl moieties have 1 to 6 carbon atoms, and the alkyl and aryl moieties are optionally substituted by one or more halogeno selected from fluoro, chloro and bromo;

$R^1$ is hydrogen or alkyl, aryl, or aralkyl wherein the aryl moieties are phenyl or naphthyl, the alkyl moieties have from 1 to 6 carbon atoms, and the alkyl and aryl moieties are optionally substituted by one or more halogeno selected from fluoro, chloro and bromo;

$R^2$, $R^3$ and $R^5$ which may be the same or different is each hydrogen or alkyl, hydroxy, alkoxy, carboxy, alkyloxycarbonyl, halogeno selected from fluoro, chloro, bromo, aryl, or aryloxycarbonyl wherein the aryl moieties are phenyl or naphthyl, the alkyl moieties have 1 to 6 carbon atoms, and the aryl moieties are optionally substituted by one or more halogeno selected from fluoro, chloro and bromo; or a physiologically acceptable salt thereof.

7. A compound as claimed in claim 6 wherein R, $R^1$, $R^2$, $R^3$, $R^4$, $R^5$ are each hydrogen, X is a $C_3$ straight-chain mono-unsaturated hydrocarbyl group and Y is a phosphonic acid.

8. A compound as claimed in claim 6 wherein X is a $C_3$ straight chain saturated or unsaturated hydrocarbyl group.

9. A compound as claimed in claim 8 wherein X is mono-unsaturated.

10. A compound as claimed in claim 9 wherein R, $R^1$, $R^2$, $R^3$, $R^4$, $R^5$ are each hydrogen, X is a $C_3$ straight-chain mono-unsaturated hydrocarbyl group and Y is a phosphonic acid or an ester thereof.

11. A compound as claimed in claim 10 wherein the unsaturated bond in the hydrocarbyl group X is located between the two carbon atoms furthest from the piperazine ring.

12. A compound as claimed in claim 6 wherein Y is a phosphonic acid or ester thereof.

13. A compound as claimed in claim 6 in which R, $R^1$, $R^2$, $R^3$, $R^4$ and $R^5$ are each hydrogen.

14. A compound of the formula:

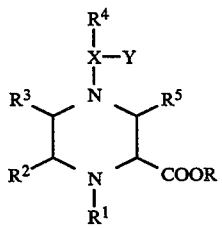

wherein X is $C_1$–$C_4$ straight chain saturated or mono-unsaturated hydrocarbyl, $R^4$ and Y are situated in any position in X and wherein at least one of the hydrogen atoms in X can be a heavy isotope of hydrogen;

$R^4$ is hydrogen or alkyl, alkoxy, hydroxy, aryl, aryloxy, aralkyl, aralkoxy, aralkylamino, or morpholino wherein the aryl moieties are phenyl or naphthyl, the alkyl moieties have from 1 to 6 carbon atoms, and the alkyl and aryl moieties are optionally substituted by one or more halogeno selected from fluoro, chloro and bromo; and Y is selected from:

 IIa or

 IIb

 IIc or

 IId or

 IIe where $R^6$ and $R^7$, which may be the same or different, is each hydrogen or alkyl, aryl, or aralkyl, wherein the aryl moieties are phenyl or naphthyl, the alkyl moieties have 1 to 6 carbon atoms, and the alkyl and aryl moieties are optionally substituted by one or more halogeno selected from fluoro, chloro and bromo, or Y is a 6-uracil residue; or $R^4$—X—Y represents —CO—$R^8$ wherein $R^8$ is saturated or unsaturated $C_1$-$C_6$ aliphatic hydrocarbyl, phenyl or naphthyl, optionally substituted by one or more halogeno selected from fluoro, chloro and bromo, carboxy, hydroxy or $C_1$–$C_6$ alkoxy;

R is hydrogen or alkyl, aryl or aralkyl wherein the aryl moieties are phenyl or naphthyl, the alkyl moieties have 1 to 6 carbon atoms, and the alkyl and aryl moieties are optionally substituted by one or more halogeno selected from fluoro, chloro and bromo;

$R^1$ is hydrogen or alkyl, aryl, or aralkyl wherein the aryl moieties are phenyl or naphthyl, the alkyl moieties have from 1 to 6 carbon atoms and the alkyl and aryl moieties are optionally substituted by one or more halogeno selected from fluoro, chloro and bromo;

$R^2$, $R^3$ and $R^5$ which may be the same or different is each hydrogen or alkyl, hydroxy, alkoxy, carboxy, alkyloxycarbonyl, halogeno selected from fluoro, chloro, bromo, aryl, or aryloxycarbonyl wherein the aryl moieties are phenyl or naphthyl, the alkyl moieties have 1 to 6 carbon atoms, and aryl moieties are optionally substituted by one or more halogeno selected from fluoro, chloro and bromo; or a physiologically acceptable salt thereof.

* * * * *